: US010234473B2

(12) United States Patent
Steuerwald et al.

(10) Patent No.: US 10,234,473 B2
(45) Date of Patent: *Mar. 19, 2019

(54) ANALYTICAL DEVICE FOR AUTOMATED DETERMINING OF A MEASURED VARIABLE OF A LIQUID SAMPLE

(75) Inventors: Ralf Steuerwald, Eberdingen (DE); Ulrich Kathe, Ludwigsburg (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 1052 days.

This patent is subject to a terminal disclaimer.

(21) Appl. No.: 13/394,562

(22) PCT Filed: Aug. 17, 2010

(86) PCT No.: PCT/EP2010/061952
§ 371 (c)(1),
(2), (4) Date: Mar. 7, 2012

(87) PCT Pub. No.: WO2011/029698
PCT Pub. Date: Mar. 17, 2011

(65) Prior Publication Data
US 2012/0173164 A1    Jul. 5, 2012

(30) Foreign Application Priority Data
Sep. 9, 2009  (DE) .................. 10 2009 029 305

(51) Int. Cl.
*G01N 35/08* (2006.01)
*G01N 35/00* (2006.01)

(52) U.S. Cl.
CPC ........ *G01N 35/08* (2013.01); *B01L 2200/028* (2013.01); *G01N 2035/00326* (2013.01)

(58) Field of Classification Search
CPC .... B01L 2200/028; G01N 2035/00326; G01N 35/00
USPC .............. 422/68.1, 81, 509; 436/43; 702/25; 73/61.59, 863.01
See application file for complete search history.

(56) References Cited

U.S. PATENT DOCUMENTS 6,887,429 B1    5/2005  Marshall
9,086,156 B2 *  7/2015  Zachmann ......... G01N 35/1097
(Continued)

FOREIGN PATENT DOCUMENTS

CN   101208593 A   6/2008
CN   101454653 A   5/2009
(Continued)

OTHER PUBLICATIONS

International Search Report.
German Search Report.
English translation of the IPER.

*Primary Examiner* — Lyle Alexander
*Assistant Examiner* — Bryan Kilpatrick
(74) *Attorney, Agent, or Firm* — Christopher R. Powers; PatServe

(57) ABSTRACT

An analytical device for automated determining of a measured variable of a liquid sample comprises: a liquid storage, which includes one or more liquid containers for one or more liquids; a measuring cell for accommodating the liquid sample, especially a liquid sample, to which has been added one or more liquids from the liquid storage, and a measuring arrangement for providing one or more measurement signals correlated with the measured variable; an electronics unit, which includes a control unit for control of the analytical device and for determining the measured variable based on the measurement signals provided by the measuring arrangement; and a handling unit including a supply- and dosing, or metering, system for supplying and metering the liquid sample and liquids from the liquid storage into the measuring cell, wherein the analytical device includes at least one exchangeable cassette, into which are integrated at least parts of the liquid storage and/or at least parts of the handling unit.

23 Claims, 3 Drawing Sheets

(56) References Cited

U.S. PATENT DOCUMENTS

| | | |
|---|---|---|
| 2004/0096347 A1 | 5/2004 | Pelmulder |
| 2005/0214165 A1* | 9/2005 | Babel et al. ............ 422/63 |
| 2006/0159587 A1 | 7/2006 | Fechtner |
| 2007/0217933 A1 | 9/2007 | Haser |
| 2008/0233634 A1 | 9/2008 | Okada |
| 2009/0293645 A1 | 12/2009 | Steuerwald |
| 2011/0212859 A1* | 9/2011 | O'Banion ......... B01L 3/545 |
| | | 506/13 |
| 2012/0285224 A1* | 11/2012 | Zachmann et al. ...... 73/64.56 |
| 2013/0243651 A1* | 9/2013 | Oprea et al. ............ 422/63 |

FOREIGN PATENT DOCUMENTS

| | | |
|---|---|---|
| CN | 101482571 A | 7/2009 |
| DE | 10210051 A1 | 10/2003 |
| DE | 10227032 A1 | 11/2003 |
| DE | 10222822 A1 | 12/2003 |
| DE | 10246211 A1 | 4/2004 |
| DE | 102005055284 A1 | 5/2007 |
| DE | 69934506 T2 | 9/2007 |
| DE | 102006049347 A1 | 4/2008 |
| EP | 0832182 B1 | 4/1998 |
| EP | 1029554 A2 | 8/2000 |
| EP | 1286720 B1 | 3/2003 |
| EP | 1624303 A2 | 2/2006 |
| EP | 1820967 A1 | 8/2007 |
| WO | WO 99/33559 | 7/1999 |
| WO | WO 03/096027 A1 | 11/2003 |
| WO | WO 2006/115663 A2 | 11/2006 |
| WO | WO 2007/137119 A2 | 11/2007 |
| WO | WO 2008/013813 A2 | 1/2008 |
| WO | WO2009/062938 A1 | 5/2009 |
| WO | WO 2011/029698 A1 | 3/2011 |

* cited by examiner

Stand der Technik

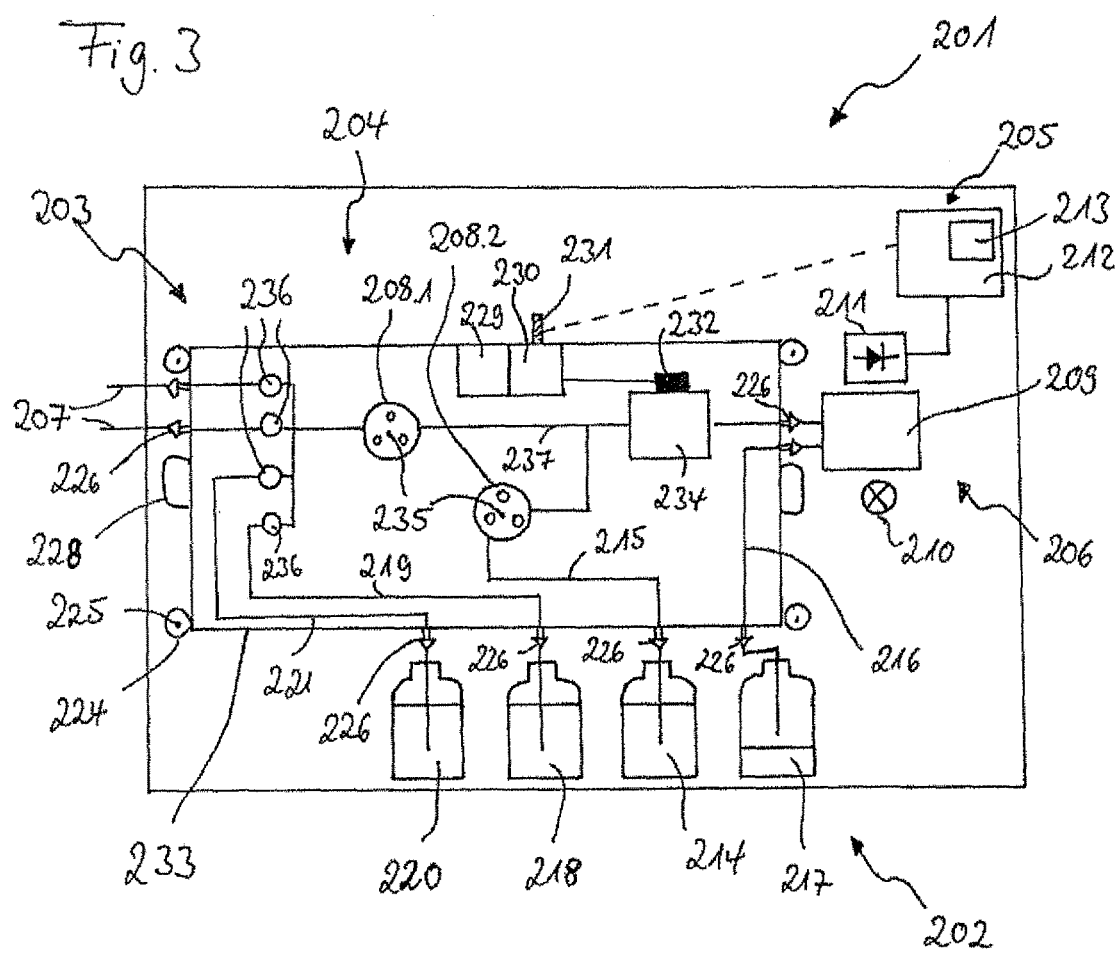

ANALYTICAL DEVICE FOR AUTOMATED DETERMINING OF A MEASURED VARIABLE OF A LIQUID SAMPLE

TECHNICAL FIELD

The invention relates to an analytical device for automated determining of a measured variable of a liquid sample.

BACKGROUND DISCUSSION

Such analytical devices are applied, for example, in process measurements technology or in industrial measurements technology. For example, analytical devices can serve for monitoring and optimizing the cleaning effectiveness of a clarification plant, in monitoring the activation basin and the clarification plant outlet or in the case of the control of additive metering. Furthermore, analytical devices can be applied for monitoring drinking water or for quality monitoring of food. Measured and monitored are, for example, the content of a sample as regards special substances, for example, ions such as ammonium, phosphate or nitrate, or biological or biochemical compounds, e.g. hormones, and even microorganisms.

Frequently in analytical devices, one or more reagents are added to the sample to be analyzed, so that a chemical reaction occurs in the liquid sample. Preferably, the reagents are so selected that the chemical reaction can be followed by means of physical methods, for example, by optical measurements. For example, the chemical reaction can effect a color change, which is detectable photometrically, thus with optical means.

In order to use such analytical methods in an automated manner, for example, in industrial applications, it is necessary to provide an analytical device, which performs the required analytical method in an automated manner. The most important requirements for such an analytical device are, besides sufficient accuracy of measurement, robustness, simple serviceability and the assurance of a sufficient working, and environmental, safety. Since the reagents used for analysis are sometimes not dischargeable into the water system, their safe disposal plays likewise an essential role.

From the state of the art, there are already semiautomatic and automatic analytical devices known. These are often relatively complicated in construction and, consequently, susceptible to malfunctions, and, as a rule, only serviceable by trained technicians. Thus, for example, DE 102 22 822 A1 and DE 102 20 829 A1 disclose online analyzers for analyzing measurement samples. The online analyzers are, in each case, embodied as cabinet devices, in which are arranged a control unit, reagent supply containers, pumps for conveying and dosing, or metering, reagents into a mixing cuvette for mixing the reagents with the liquid, a waste container, as well as an optical unit for optical measurements on the liquid sample treated with reagents in the mixing cuvette. The reagents are supplied via hose linkages from the reagent containers into the mixing cuvette. Correspondingly, used liquid is transferred from the mixing cuvette, in turn, via a hose linkage into the waste container. If the waste container or one or more of the reagent supply containers must be replaced, attention must be paid that the hose linkages are then correctly reconnected. The hoses and the supply pumps are susceptible to material fatigue and must likewise be subjected to maintenance or replaced from time to time.

SUMMARY OF THE INVENTION

It is therefore an object of the invention to provide an analytical device, which overcomes the disadvantages of the state of the art. Especially, the analytical device should satisfy the requirements for use in process measurements technology, i.e. it should be robust, cost effective and simple to service and maintain, especially also the danger of contamination of a service person and, respectively, the environment should be avoided.

The object is achieved by an analytical device for automated determining of a measured variable of a liquid sample, wherein the analytical device comprises:

a liquid storage, which includes one or more liquid containers for one or more liquids;

a measuring cell for accommodating the liquid sample, especially a liquid sample, to which has been added one or more liquids from the liquid storage, and a measuring arrangement for providing one or more measurement signals correlated with the measured variable;

an electronics unit, which includes a control unit for control of the analytical device and for determining the measured variable based on the measurement signals provided by the measuring arrangement;

a handling unit including a supply and dosing, or metering, system for supplying and metering the liquid sample and liquids from the liquid containers into the measuring cell, wherein the analytical device includes at least one exchangeable cassette, into which are integrated at least parts of the liquid storage and/or at least parts of the handling unit.

The liquid containers of the liquid storage can be, for example, supply containers, in which consumable liquids are held, such as e.g. reagents for mixing and, in given cases, chemical reaction with the liquid sample, standard liquid for calibrating or rinsing liquid. The liquid containers of the liquid storage can furthermore include at least one waste container for accommodating used liquids.

The cassette can possess a housing, which seals the cassette interior relative to the environment except for one or more connectors, via which fluid connections between liquid lines or liquid containers within the cassette and liquid lines or liquid containers outside the cassette can be formed. Preferably, these connections are closable liquid tightly.

The terminology "fluid connection between two components" means here and in the following a structural connection between the components, via which a fluid, preferably a liquid, can be transmitted from the first component to the second component. Especially, it should not be excluded that additional components are arranged between the first and the second component, which stand in fluid connection. A fluid connection is furthermore especially sealed in such a manner that a loss free transmission of the fluid between the first and the second components is possible.

The terminology "exchangeable cassette" means a cassette, which via one or more connections can be connected with at least one additional unit of the analytical device, especially with the liquid containers, with the handling unit, especially with the supply- and dosing system, with the measuring cell and/or with the electronics unit, and then later can be disconnected from such, and replaced a cassette of the same type. Cassettes of the same type have equal connections, so that each such cassette can be connected releasably with the additional unit without further modification of the analytical device. Preferably, same type cassettes also possess a housing having essentially identical geometry, especially with essentially identical dimensions.

Therewith, same type cassettes have the same space requirement, and so can replace one another without other changes of the remaining analytical device construction. Cassettes of the same type can, however, differ from one another, especially as regards the number of contained liquid containers, the type of liquids contained in the liquid containers, the number of liquid lines provided in the cassette, especially also as regards the embodiment of the courses of the liquid lines of the handling unit, for example, the number of branchings between liquid lines. Thus, for example, an entire series of same type cassettes can exist, in which at least parts of a liquid storage or at least parts of a handling unit or both at least parts of the liquid storage as well as also at least parts of the handling unit together are integrated, which are designed for very different analytical methods, but which, as regards their connections and their space requirement are essentially identical. These different cassettes can, via their same type connections, be installed directly in one and the same analytical device construction, for example, in a predetermined chamber basic structure of an analytical device embodied as a cabinet device, and, when required, be replaced, one for the other. In this way, there is available to the manufacturer a "kit of building blocks", from which to build a large number of combinations of consumable liquids and handling options.

Also, such a construction is advantageous for the user of the analytical device, since it limits the maintenance effort significantly: especially, the integration of the liquid storage into an exchangeable cassette permits, in a very simple manner, changing of the liquid storage, when, for example, one or more supply containers for consumable liquids are completely or almost completely emptied following the performing of a series of analytical measurements, or when a waste container can accommodate no more liquid. The cassette can then be replaced by a new, same type cassette with completely filled supply containers, and, respectively, empty waste containers. In this way, the replacement of consumable liquids is very much simplified, since a service person only needs to replace the cassette, without having to be involved directly with chemicals, or having to pay attention that the right connections are made to the right liquid containers. Also the maintenance of the handling unit is significantly facilitated, since wear parts of the handling unit, especially the dosing, metering- and supply system, such as e.g. hoses serving as liquid lines, are provided in an exchangeable cassette. When the wear parts need to be replaced by new ones, a service person need only replace the cassette with a new, same type cassette. In comparison with replacement of individual liquid lines, the time consumed for this is clearly smaller, while simultaneously the danger of a mismatch of the connections of the individual liquid lines is reduced.

The electronics unit can include, besides the control unit, furthermore an energy supply unit for the analytical device. The control unit can serve centrally for controlling the dosing, metering- and supply unit, of the measuring arrangement, for controlling valves, especially valves belonging to the handling unit, and for controlling further functions of the analytical device. Involved, in such case, is a data processing unit with processor and one or more memories.

The measuring arrangement is embodied to determine a measured variable of a liquid sample present in the measuring cell, in given cases, mixed with liquids from the liquid storage, or reacted chemically with reagents from the liquid storage. The measuring arrangement can be especially an optical apparatus, for example, a photometer or a spectrometer. The measuring apparatus can also be an electrochemical apparatus, for example, an ion-selective electrode. The measuring arrangement generates measurement signals. In the case of an optical apparatus, which, as a rule, includes a radiation source and a photoelectric receiver, the measurement signals are, in such case, for example, electrical current- or voltage signals, which are output by the receiver in correlation with the received radiation intensity. In the case of an ion-selective electrode, a voltage signal correlated with the potential established on an ion-selective membrane of the electrode is output. These measurement signals are received by the control unit and further evaluated, in order to ascertain therefrom a measured value of the measured variable to be determined for the current liquid sample.

The handling unit can include, besides the supply- and dosing system, which is used both for metering the liquid sample as well as also for metering liquids, especially reagents, to be mixed with the liquid sample, also a mixing cell and a reaction cell for carrying out a chemical reaction between one or more reagents and the liquid sample. Thus, an analytical device for determining the chemical oxygen demand of a liquid sample includes, for example, a heatable reaction cell, in which a reacting of the liquid sample with an oxidizing agent can be performed. The handling unit can furthermore include heating means, cooling elements, especially thermoelectric elements or heat pipes. The supply- and dosing system can, for example, include one or more peristaltic pumps, also referred to as hose, or tube, pumps, or one or more syringe pumps. Correspondingly, the handling unit, and, respectively, the supply- and dosing system, includes a series of liquid lines, which especially can be embodied as hoses, and corresponding connections of the liquid lines to liquid containers of the liquid storage, or to the measuring cell, mixing cell or reaction cell or other functional elements provided in the handling unit.

In an embodiment, the analytical device can include a structural framework, with which the (at least one) exchangeable cassette is releasably connected. The structural framework determines the position of the exchangeable cassette within the analytical device. Thus, it is assured that the cassette is always located in the position provided for the intended use of the analytical device relative to the other parts of the apparatus, especially relative to possibly present, additional exchangeable cassettes. The measuring arrangement and the electronics unit with the control unit are preferably integrated into the structural framework, i.e. not a component of an exchangeable cassette.

In an advantageous embodiment, the at least one exchangeable cassette can include a data processing unit, wherein the data processing unit can include especially a data memory and a microprocessor, which are integrated in a housing of the exchangeable cassette. As is explained below, such a "mobile" data processing unit within the cassette can be used to process measurement signals of sensors provided in the cassette. Stored in the memory of the data processing unit can be data, which include information concerning the cassette. For example, stored in the data memory can be which type of cassette it involves, e.g. a cassette with parts of a handling unit or a cassette with liquid containers of the liquid storage. Furthermore, stored can be the analytical method, for which the cassette is suitable, for example, for determining a chemical substance in the liquid sample or for determining the chemical oxygen demand of the liquid sample. Other data in the data memory can concern the last maintenance of the cassette, the volume and the concentration of reagents contained in liquid containers or information concerning the probable next point in time, when the cassette must be replaced or maintained.

The data processing unit can include an interface, via which an, especially wireless, communication of the data processing unit with a superordinated unit is possible, especially with the control unit of the analytical device, an external servicing device or a process control station. The communication can occur, for example, via an RFID-, GSM-, WLAN- or Bluetooth interface.

The control unit of the analytical device can be designed, upon replacement of the cassette, e.g. after the cassette has been connected with the structural framework of the analytical device and so is arranged in its defined position in the analytical apparatus, automatically or due to an input by a service person, to read out data stored in the data memory of the data processing unit of the cassette, e.g. the above named data.

In an alternative, simpler form of embodiment, identifying data of the cassette can be stored in an RFID-chip or in an optically out-readable code, for example, a barcode, which is secured on the cassette. By means of a reading device belonging to the analytical device, the identifying data can, in the case of replacement of the cassette, either be read-out automatically or upon an input of a service person and forwarded to the control unit.

For facilitating installation of the cassette into its defined position in the analytical device, the at least one cassette can include guiding means, which interact with complementary guiding means of the structural framework or complementary guiding means of at least one additional cassette of the analytical device.

Fundamentally, the cassette can include, for example, the entire handling unit. When it becomes necessary to replace wear parts of the handling unit, for example, hoses serving as liquid lines, the entire cassette can be replaced by an identically embodied, new cassette. Since the handling unit includes, however, also components not requiring maintenance, especially also expensive components, for example, drives of the supply- and dosing, or metering, unit, parts of pumps of the supply- and dosing, or metering, unit, among other things, it is, in this case, preferable to recondition a replaced cassette, e.g. by replacing the wear parts. This reconditioning can be performed by the manufacturer of the analytical device or by specially trained personnel of the user of the analytical device. Advantageous, however, is an embodiment, in which the exchangeable cassette includes maintenance requiring parts or wear parts of the handling unit, especially hoses, and wherein non maintenance requiring parts of the handling unit, especially drives or drive shafts, are secured to the structural framework of the analytical device. In this case, a replaced cassette can be disposed of without need for reconditioning. In the case of this embodiment, it is especially advantageous, when the different wear parts contained in a cassette, for example, through corresponding choice of material, are so designed that they possess comparable lifetimes.

In an additional embodiment, supplementally, the measuring cell is integrated into the at least one exchangeable cassette.

When at least two liquid containers of the liquid storage are integrated into the exchangeable cassette, the cassette can have a housing surrounding the liquid containers, wherein, in a wall of the housing, connections are integrated, which interact with complementary connections of the handling unit, in order to connect the liquid containers integrated in the cassette fluidically with liquid lines of the handling unit. In the case of this embodiment, a number of liquid containers can be connected to the handling unit without additional effort.

It is especially advantageous, when the connections, in each case, have a closure opening or a valve opening, which is embodied in such a manner that it, in the case of connecting the liquid containers with the handling unit, automatically opens, and, in the case of isolating the liquid containers from the handling unit, automatically closes. Assuming that the cassette has, besides the said connections, no additional openings, which connect the interior of the cassette, especially the liquid containers, and the environment with one another, the cassette is then completely closed off in the state isolated from the analytical device, so that no liquids can escape into the environment. In this way, a contamination of a service person or the environment is prevented in the case of removing, and in the case of transporting, the cassette. It is very advantageous for the shipment of new reagents for the analytical device from the manufacturer to the user of the analytical device, when all liquid containers are integrated in such a cassette. The reagents can then be sent to the user already in the cassette. The user need then only connect the cassette to the handling unit. Due to the closure, or valve, openings of the connections, there is then no danger that the reagents can escape into the environment. The used cassette with empty supply containers and filled waste containers can, in corresponding manner, be sent back without danger from the user to the manufacturer for disposal, or for refilling.

Alternatively, it is also possible that the user refills the required reagents into the cassette and disposes of wastes collected in the cassette. For this purpose, additional openings can be provided in the housing of the cassette. Such openings can likewise be closable by closures or valves.

The handling unit can include an adapter, which affixes the complementary connections of the handling unit spatially in such a manner that they interact with the connections integrated in the wall of the housing of the cassette, when the cassette is located in its intended position within the analytical device. In this way, a mismatch of the connections between the liquid containers and the corresponding liquid lines of the handling unit is excluded.

In an additional embodiment of the analytical device, in at least one of the liquid lines of the handling unit fluidically connected with connectors of the cassette, especially in a liquid line between the complementary connectors of the handling unit and the supply- and dosing system, a media detector, especially a light barrier, is arranged. In this way, metering of the liquid into the measuring cell, or into, in given cases, present, mixing- and/or reaction cells, can be monitored.

The cassette can furthermore include at least one sensor for monitoring the cassette, which is connected with the data processing unit of the cassette for the transmission of measurement signals. For example, the sensor can be a temperature sensor or a fill level sensor, which is so arranged that it registers the fill level in at least one liquid container. The sensor signals or measured values derived by the data processing unit from the sensor signals can be transmitted to the control unit of the analytical device. The control unit can, based on the measured values, ascertain when a maintenance measure, especially when the replacement of the cassette, is required. In the simplest case, this can occur based on a threshold value comparison. The control unit can also apply methods for predictive diagnosis, i.e. for determining a maintenance point in time in the future.

Furthermore, the control unit can be embodied automatically to perform an initializing routine following a replacement of the cassette, wherein the initializing routine especially includes at least one of the following steps:

Cleaning liquid contacting components of the handling unit and the measuring cell;
performing at least one calibration measurement;
adjusting the analytical device; and
filling liquid lines of the handling unit by supplying consumable liquid from liquid containers connected with the liquid lines.

Liquid contacting components of the handling unit include, especially, the liquid lines, possibly present mixing- or reaction cells, and the measuring cell. For performing a calibration measurement, a standard calibrating liquid can be supplied from the liquid storage into the measuring cell.

BRIEF DESCRIPTION OF THE DRAWINGS

The invention will now be explained in greater detail based on the illustrated examples of embodiments in the drawing, the figures of which show as follows:

FIG. 3 is a schematic representation of a second example of an embodiment of an analytical device with an exchangeable cassette, into which parts of the handling unit of the analytical device are integrated.

DETAILED DISCUSSION IN CONJUNCTION WITH THE DRAWINGS

Figure 1:
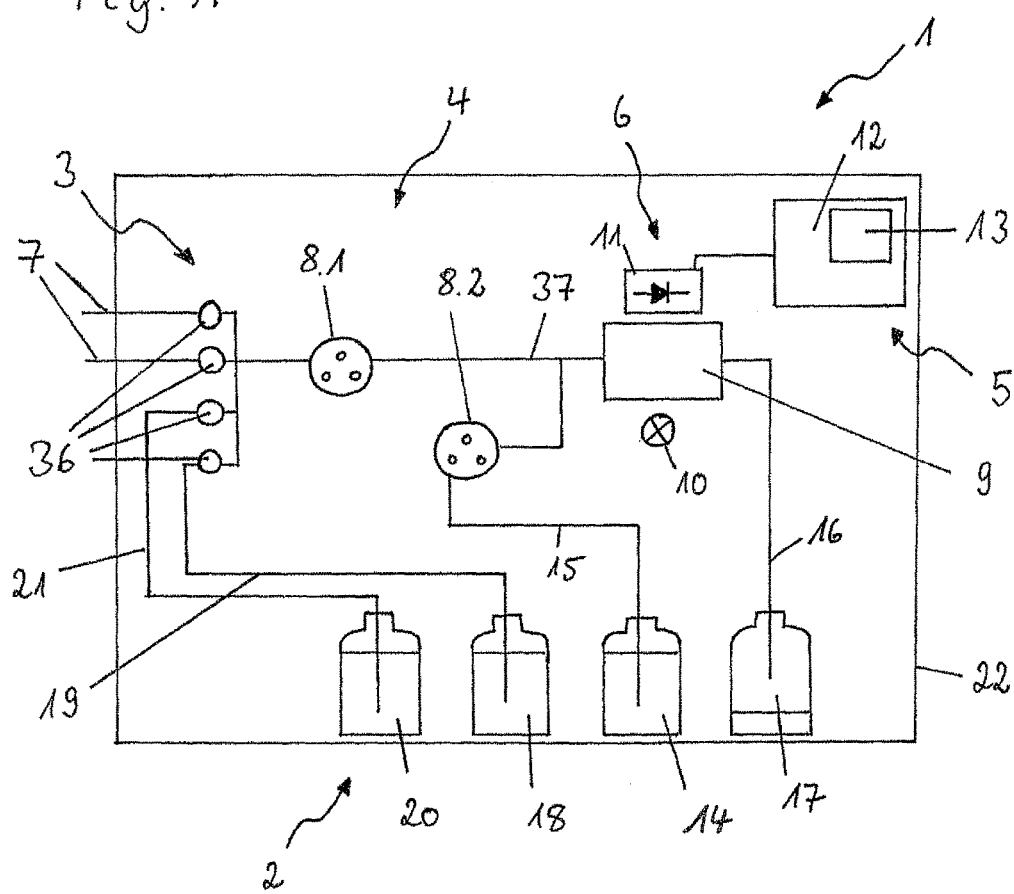
FIG. 1 is a schematic representation of an analytical device according to the state of the art.

FIG. 1 shows schematically an analytical device 1 according to the state of the art. The analytical device 1 includes a liquid storage 2 having individual liquid containers 14, 17, 18, 20, a handling unit 3 having a supply- and dosing system 4, an electronics unit 5 with a control unit 12, and an optical measuring arrangement 6. From a sample supply (not shown), for example, a clarification basin or from a water line, via the liquid lines 7, a liquid sample can be supplied by means of the supply- and dosing system 4, which, in the illustrated example, includes two peristaltic pumps 8.1 and 8.2, into the handling unit 3. The peristaltic pump 8.1 can transport the liquid sample further via the liquid line 37 into the measuring cell 9. The liquid container 14 contains a reagent to be mixed with the liquid sample. The liquid container 14 is connected via the liquid line 15 and the peristaltic pump 8.2 with the liquid line 37 for the liquid sample, so that reagent can be supplied from the liquid container 14 by means of the peristaltic pump 8.2 to the junction with the liquid line 37 and there mixed with the liquid sample, before the so formed liquid mixture is supplied into the measuring cell 9.

In the present example, the analytical device 1 is designed for photometric determinations. It includes an optical measuring arrangement 6 with a radiation source 10 and a radiation sensitive receiver 11. The radiation source 10 can be, for example, a radiation source, which emits radiation in the UV/visible spectral range, e.g. a flash lamp or a light-emitting diode emitting in such spectral range. The receiver can include, for example, one or more photodiodes. The radiation source 10 and the receiver 11 lie opposite one another arranged on opposing sides of the measuring cell 9, so that a measuring path extends between the radiation source 10 and the receiver 11 through the liquid mixture accommodated in the measuring cell 9. Such liquid mixture includes the liquid sample, the reagent supplied from the liquid container 14 and, in given cases, reaction products of a substance contained in the liquid sample with the reagent.

The analytical device 1 includes furthermore an electronics unit 5 with a control unit 12. The control unit 12, on the one hand, evaluates signals of the measuring arrangement 6, especially measurement signals of the receiver 11, and, on the other hand, also controls the photometric measuring arrangement 6. Furthermore, the control unit 12 serves also for controlling the handling unit 3, for example, for controlling the supply- and dosing system 4, e.g. the peristaltic pumps 8, or for controlling valves 36 of the handling unit 3. For output of measurement signals, the control unit 12 includes a display 13. A service person can read off data via the display 13 and can service the control unit 12, and therewith the analytical device 1, via an input unit (not shown).

The measuring cell 9 is connected via a liquid line 16 with a liquid container 17. After performing the measuring, the liquid mixture in the measuring cell 9 can be drained as waste via the liquid line 16 into the liquid container 17.

The analytical device includes an additional liquid container 18, which is connected via a valve 36 and the peristaltic pump 8.1 with the liquid line 37 to the measuring cell 9. Liquid container 18 contains a cleaning liquid, which, for cleaning the liquid contacting parts of the analytical device 1, can be supplied by means of the peristaltic pump 8.1 via the liquid line 19 into the other liquid lines of the analytical device and via the measuring cell 9 into the liquid container 17. A further liquid container 20 of the analytical device contains a standard liquid for calibration measurements. This liquid container 20 is connected via a liquid line 21, a valve 36 and the peristaltic pump 8.1 with the liquid line 37, which leads to the measuring cell 9. Calibration measurements can be regularly performed by supplying from the liquid container 20 standard liquid via the liquid line 21 by means of the peristaltic pump 8.1 as liquid sample, in given cases, together with the reagent present in the liquid container 14, into the measuring cell 9. Based on the calibration measurements, an adjusting of the analytical device 1 can be performed.

The analytical device 1 includes a housing 22, which surrounds and protects the individual parts of the analytical device, especially the handling unit 3, the electronics unit 5 and the liquid storage 2. This is especially advantageous, when the analytical device 1 is to be operated outside. The housing 22 can be embodied especially as a cabinet having at least one door.

Besides regular calibration measurements and adjustments, in the case of the here described analytical device 1, a series of further maintenance measures are regularly required: Thus, for example, the liquid containers 14, 18 and 20 for reagent, cleaning liquid and standard liquid for calibrating must be regularly refilled or replaced. Correspondingly, also the liquid container 17 for waste must be regularly emptied or replaced. In such case, attention must be paid that emptied, refilled or replaced liquid containers are reconnected with the right liquid lines 15, 16, 19 and 21. In the case of exchange, emptying or refilling of the liquid container 14, 18, 20 and 17, there is, furthermore, the danger of a contamination of the service person or the environment.

Liquid lines 7, 15, 16, 19 and 21, which in the here illustrated example, are embodied as hoses for the operation with a peristaltic pump 8, are subject to material aging and must therefore likewise be replaced at regular intervals. Also here, attention is to be paid that, in the case of replacement of the liquid lines, no mixups of the connections to the peristaltic pumps 8 and to the liquid containers 14, 17, 18 and 20 occur. Furthermore, is, in the connecting of new hoses, attention is to be paid that these are connected, sealed to liquid leakage, with the corresponding connectors of the liquid containers 14, 17, 18 and 20, the measuring cell 9 or with one another for forming branching locations. Reagents still present in the liquid lines 7, 15, 16, 19 and 21 at the point in time of replacement can lead to contamination of the service person and the environment.

After replacement of liquid containers and/or lines, the service person must perform an initializing of the analytical device. This initializing includes at least the filling of the liquid lines, so that liquid is supplied by means of the peristaltic pumps 8 into each liquid line, at least, however, into the liquid lines 7 and 14 for the sample and for the reagent.

All these measures are not only associated with much time consumed, they also require a well trained service person. In the following, two examples of embodiments for analytical devices of the initially described type will now be explained, in the case of which these maintenance measures are not required or at least are significantly simplified for the service person.

Figure 2:
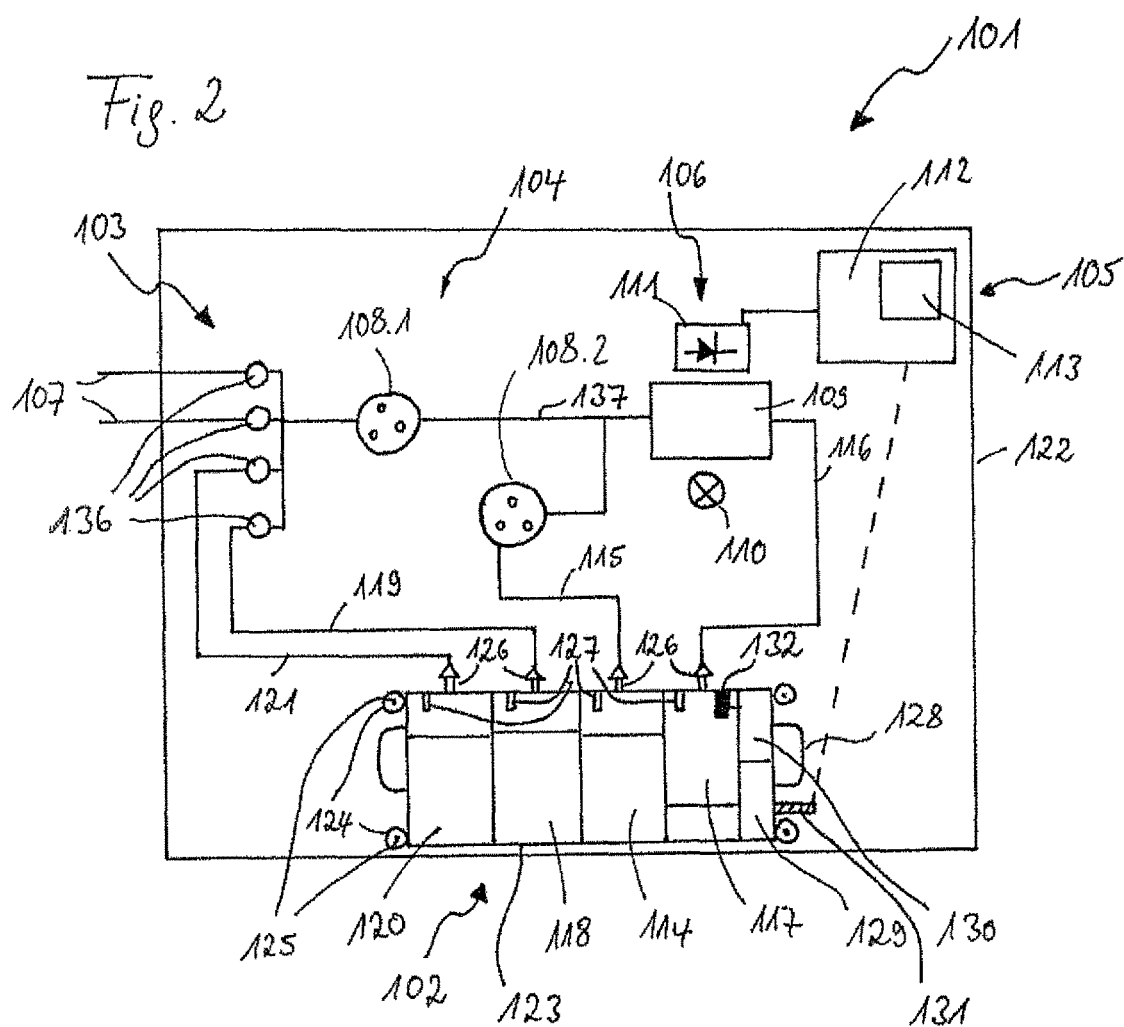
FIG. 2 is a schematic representation of a first example of an embodiment of an analytical device with an exchangeable cassette, into which the liquid storage of the analytical device is integrated.

FIG. 2 shows a schematic representation of an analytical device 101, in the case of which the liquid storage 102 is integrated into an exchangeable cassette 123. The structure and operation of the analytical device 101 illustrated in FIG. 2 is otherwise basically identical with the analytical device illustrated in FIG. 1: It includes, besides the liquid storage 102, a handling unit 103 with a supply- and dosing system 104, an electronics unit 105 and an optical measuring arrangement 106. The liquid storage 102 integrated into the exchangeable cassette 123 includes four liquid containers, namely a first liquid container 114 for a reagent, a second liquid container 118 for a cleaning liquid and a third liquid container 120 for a standard solution for performing calibration measurements. By means of the peristaltic pump 108.1 of the supply- and dosing system 104, a liquid sample can be supplied from a source (not shown) via the liquid line 107 into a liquid line 137, which leads to a measuring cell 109. The liquid container 114 with the reagent is connected via a liquid line 115 and the peristaltic pump 108.2 with the liquid line 137, so that by means of the peristaltic pump 108.2 reagent can be supplied into the liquid line 137. At the junction between the liquid line 137 and the liquid line 115, there occurs a mixing of the liquid sample and the reagent, before the so formed liquid mixture is supplied into the measuring cell 109.

The measuring arrangement 106 is embodied as the measuring arrangement 6 in the example of FIG. 1 as a photometric measuring arrangement with a radiation source 110 and a receiver 111. The radiation source 110 and the receiver 111 lie opposite one another on opposing sides of the measuring cell 109, so that between the radiation source 110 and the receiver 111 a measuring path extends through the liquid mixture accommodated in the measuring cell 109. Evaluation of the measurement signals of the measuring apparatus 106 for determining a measured variable of the liquid sample occurs by way of the control unit 112. The control unit 112 controls, moreover, the handling unit 103, e.g. the supply- and dosing system 104, especially the peristaltic pumps 108 and valves 136 of the handling unit 103. The control unit 112 has a display 113 for display of measured values and other data. Furthermore, the control unit has an input function, e.g. a rotate-press switch, for servicing the control unit 112. The measuring cell 109 is connected via a liquid line 116 with a liquid container 117 serving as waste container. By means of the dosing, metering- and supply system 104, after a measuring, the liquid mixture can be drained via the liquid line 116 from the measuring cell 109 into the liquid container 117.

A further liquid container 118, which contains cleaning liquid, is connected, via a liquid line 119, a valve 136 and the peristaltic pump 108.1, with the liquid line 137 and the measuring cell 109. For cleaning the liquid contacting components of the analytical device 101, the cleaning liquid can be supplied from the liquid container 118 by means of the peristaltic pumps 108 via the liquid line 119 into the handling unit 103 and therewith rinse/wash the measuring cell 109. The control unit 112 controls the valves 136 correspondingly for this purpose, so that the peristaltic pump 108.1, instead of supplying the liquid sample via the line 107, supplies the cleaning liquid via the liquid line 119. For calibration measurements, the standard liquid contained in liquid container 120 can correspondingly be supplied via the liquid line 121 into the measuring cell 109. Used cleaning- or standard liquid can then be drained via the liquid line 116 into the liquid container 117.

The analytical device 101 has a housing 122, which surrounds the individual parts of the analytical device 101, especially the handling unit 103, the electronics unit 105 and the measuring arrangement 106. Housing 122 serves, on the one hand, for protecting the analytical device, for example, against the influences of weather, when the analytical device 101 is applied outside. On the other hand, housing 122 serves also as a structural framework, on which the individual components and functional elements of the analytical device 101 are secured. For this, the housing 122 can have additional support walls, support plates or struts in its interior.

In the example of FIG. 2, the liquid containers 120, 118, 114 and 117 are integrated into a cassette 123. Cassette 123 includes a housing, which surrounds the liquid containers 120, 118, 114 and 117 and essentially seals liquid tightly relative to the environment. Preferably, chambers are formed in the housing of the cassette 123, which serve as liquid containers, or in which inserts serving as liquid containers can be accommodated. The cassette with its housing can be introduced into the housing 122 of the analyzer 101 and arranged and secured in an intended position, i.e. with a predetermined orientation relative to the other elements of the analyzer 101, especially the handling unit 103. In order to assure the maintaining of the intended position of the cassette 123, the cassette has on its sides guiding means 124, which can be embodied, for example, as guiding rails or as hollow cylinders. These engage in complementary guiding means 125 of the structural framework of the housing 122, e.g. guides or rods, and interact with these. For easier insertion or removing of the cassette 123 into the structural framework or from the structural framework of the housing 122, grips 128 can be provided on the sides of the cassette housing.

For connecting the liquid containers 114, 117, 118 and 120 to the liquid lines 115, 116, 119 and 121, the cassette 123 includes connectors 126, which can be embodied, for example, as hose connectors mounted fixedly in the housing wall of the cassette 123, and which connect, in each case, the interior of a liquid container 114, 117, 118 and 120 with, in each case, the associated liquid line 115, 116, 119 and 121 of the handling unit 103. The hose connectors can have, advantageously, in each case, a closure opening or a valve opening, which opens preferably automatically, upon the connecting of the liquid lines 115, 116, 119 and 121, and correspondingly recloses, upon the separating of the liquid lines 115, 116, 119 and 121. It is also an option that valves be provided, which a service person can manually close before separating the liquid lines 115, 116, 119 and 121 from the connectors 126 and correspondingly can manually open after the reconnecting. In this way, it is prevented that liquids escape from the cassette 123 removed from the analytical device 101. Optionally, the cassette can have additional, likewise automatically or manually closable, filling openings 127 for refilling liquids into the liquid containers 114, 118 and 120.

The cassette 123 contains, furthermore, a data processing unit with a microprocessor 129 and a memory 130, in which data and/or programs can be stored. In the memory 130, data can be stored, which include information concerning the cassette 123. For example, there can be stored, which type of cassette it is. Furthermore, there can be stored, for which analytical method the cassette is suitable, for example, for determining a chemical substance in the liquid sample or for determining the chemical oxygen demand of the liquid sample. Other data in the data memory can concern the last maintenance of the cassette 123, the volume and concentration of the reagent or of the standard liquid for calibrating, storability data for the liquids or information concerning the probable next point in time, at which the cassette needs to be replaced or subjected to maintenance. The data processing unit can transmit data from the data memory to the control unit 112 of the analytical device 101. For this, the data processing unit has an interface 131, via which data can be exchanged between the data processing unit of the cassette 123 and the control unit 112. This interface 131 can be implemented either hardwired or preferably wirelessly. For example, the interface can be a radio interface, especially an RFID-interface, a GSM interface or a WLAN- or Bluetooth interface.

In an alternative embodiment, the cassette 123 can, instead of a complete data processing unit with microprocessor and memory, also use a simple RFID transponder, in which the corresponding cassette data are coded. Via a reading device connected with the control unit 112 for data exchange, these data can be read-out from the RFID transponder. This embodiment is simple, but somewhat less flexible than the embodiment of the cassette 123 with integrated data processing unit.

Arranged in the liquid container 117 is a sensor 132, which is connected with the microprocessor 129 of the data processing unit. One or more such sensors can be provided in each liquid container 114, 117, 118, 120 of the liquid storage 102. The microprocessor 129 can be connected with the sensor for exchange of data, and especially process measurement signals of the sensor 132 and store the processed measurement signals or therefrom derived values in the memory 130 and/or transmit such via the interface 131 to the control unit 112. The sensor 132 can, be for example, a temperature sensor or a fill level sensor. Based on the data of the fill level sensor, it can be detected, when the liquid container 117 is filled with waste liquid to a predetermined maximum fill level stored in the data memory 130. Upon reaching this maximum fill level, the data processing unit can output a warning signal to the control unit 112. It is also an option to store in the control unit 112 a fill level-threshold value, with which the control unit 112 compares fill level measured values transmitted from the data processing unit via the interface 131. Upon reaching the threshold value, the control unit can then output a warning signal or suppress further introduction of liquid into the liquid container 117. In analogous manner, a fill level sensor can be applied, in order to monitor, when the consumable liquids contained in the liquid containers 114, 118 and 120 reach a predetermined minimum fill level.

The sensor 132 can also be a temperature sensor. Of course, also both a temperature sensor as well as also a fill level sensor can be arranged in one or more liquid containers. The measurement signals of the temperature sensor can in equal manner, as earlier described for the fill level measurement signals, be processed by the data processing unit of the cassette 123 and/or by the control unit 112. The ascertained temperature measured values over the lifetime of the cassette 123 can be stored in the memory 130 or in a memory of the control unit 112, also over time periods, within which the cassette 123 is not installed in the analytical device 101, e.g. during a transport or storage time. From these measured values, a "temperature history" of the cassette 123 can be ascertained, based on which predictions concerning the storability of the liquids contained in the liquid container 114, 118 and 120 can be made. The ascertained remaining storability can be output via the display 113 of the control unit 112.

The energy required for operating the sensors and the data processing unit can come from a central energy supply unit of the analytical device 101 or from an additional energy supply unit (not shown) integrated into the cassette 123. In the latter case, such can be especially a disposable battery or an autarkically functioning, energy supply unit, which produces electrical current, for example, from the ambient temperature, e.g. by means of a Peltier element, from vibrations, from air flows or from electromagnetic radiation, e.g. by means of solar cells.

Through the previously described integration of the liquid storage 102 into an exchangeable cassette, maintenance of the analytical device 101 simplifies significantly: If one or more of the liquid containers 114, 118 or 120 contains insufficient liquid for further measurements or the liquid container 117 can accommodate no more liquid from the measuring cell 109, this can be detected based on the measured values of the one or more sensors 132 of the control unit 112, and a warning signal can be output via the display 113 of the control unit 112. By means of predictive diagnostic routines, which are basically known from the state of the art, for example, by extrapolation of the measured values ascertained by means of the one or more sensors 132, the control unit 112 can also ascertain a point in time in the future, at which the liquid containers, in each case, must be emptied, newly filled, or replaced. In this way, a service person can timely schedule the corresponding maintenance measures.

At the corresponding point in time, the cassette 123 can be replaced with an equally embodied, new cassette 123. Advantageously, in such case, the connectors 126 sealable in the case of the removing of the cassette 123 from the housing 122 are sealed, by means of which, as already described, a contamination of the service person and the environment with liquids from the cassette 123 is prevented. Since the liquid containers are fixedly installed in the cassette, there is also no longer danger that liquid containers are wrongly placed. The used cassette 123 can be disposed of or reconditioned.

A further simplifying of the replacing of the cassette 123 can be achieved by providing that the liquid lines 115, 119, 121 and 116 to be connected with the connectors 126 of the cassette 123 have connectors complementary to the connectors 126, and the liquid line connectors are integrated in adapters connected fixedly with the structural framework of the housing 122. In this way, the connectors of the liquid lines 115, 119, 116 and 121 can be affixed spatially in such a manner that they interact with the connectors integrated in the wall of the housing of the cassette to form a fluid, especially liquid tight, connecting of the liquid containers with the associated liquid lines, when the cassette is placed in its intended position within the analytical device. The connections can be embodied in known manner in such a way that, in the connecting of the connectors 126 with the complementary connectors of the liquid lines 115, 116, 119 and 121, no leakages occur. Especially, this embodiment prevents any misplacing of the liquid lines.

After the connecting of a new cassette, the control unit 112 can read out via the interface 131 the data of the new cassette and, based on this data, reset the diagnostic routines. Furthermore, the control unit 112 can, upon the connecting of the new cassette 123, perform an initializing routine. The initializing routine can include, for example, cleaning, calibrating and/or adjusting of the analytical device 101 in the previously described manner. Furthermore, the initializing routine can include filling the liquid lines 107, 115, 119 and 121. For this, it is advantageous, when media detectors (not shown) are arranged in the liquid lines or in the region of the connectors 126. These media detectors are connected with the control unit 112. Based on the measurement signals of the media detectors, the control unit can ascertain whether the liquid lines 107, 115, 119 and 121 are filled, respectively, with sample, reagent, cleaning liquid, and standard liquid for calibrating.

FIG. 3 shows a further example of an embodiment of an analytical device 201, in the case of which parts of the handling unit 203 are integrated into an exchangeable cassette 233. The analytical device 201 is otherwise similarly constructed and includes comparable functions to the analytical devices 1 and 101 illustrated in FIGS. 1 and 2.

The liquid storage 202 of the analytical device 201 includes a liquid container 214 for reagent, a liquid container 218 for cleaning liquid and a liquid container 220 for standard liquid for calibrating. A further liquid container 217 is provided for accommodating wastes. The liquid containers and a liquid samples source (not shown), are connected via liquid lines 207, 215, 219 and 221, in given cases, via valves 236, and via the peristaltic pumps 208.1, or 208.2, with a liquid line 237, which leads to reaction cell 234. The liquid sample, the reagent, the cleaning liquid and the standard liquid can, in analogous manner as in the case of the earlier described examples of embodiments, be supplied by the peristaltic pumps 208.1 and 208.2 of the supply- and dosing system 204 into the handling unit 203, or into the liquid line 237, and further into the reaction cell 234.

The reaction cell is heatable by means of a heating element (not shown). It serves to heat a reaction mixture, which includes the liquid sample and the reagent, over a predetermined time span, in order to accelerate a chemical reaction between a component contained in the liquid sample and the reagent. For example, an oxidative decomposition of the liquid sample can be performed in the reaction cell 234. Reaction cell 234 is connected via a liquid line 235 with a measuring cell 209, so that, after the reaction terminates, the reaction mixture can be transferred into the measuring cell 209. By means of a photometric measuring arrangement 206, which includes a radiation source 210 and a receiver 211, and a control unit 212, which controls the measuring arrangement 206 and evaluates measurement signals of the measuring arrangement 206, a measured value of the measured variable to be ascertained sample can be determined for the liquid, in the manner described for the examples of embodiments above. Measuring cell 209 is connected with the liquid container 217 via a liquid line 216, so that the reaction mixture can be drained as waste into such liquid container 217 after termination of the measuring.

As in the case of the cassette 123 of the analytical device 101 of the FIG. 2, the cassette 233, into which parts of the handling unit 203 are integrated in the example of FIG. 3, also possesses a housing, which essentially seals the interior of the cassette 233 from the environment. Integrated in the housing wall are connectors 226, which are embodied, for example, as hose connectors. Connectors 226 connect the liquid lines 207, 216, 215, 219 and 221, 235 integrated into the cassette with the associated liquid containers of the liquid storage 202, with the measuring cell 209 and with the sample supply (not shown).

Likewise as in the case of cassette 123 of the analytical device 101 illustrated in FIG. 2, the cassette can be introduced into the housing 222 of the analytical device 201 and, with the assistance of guiding means 224, which interact with complementary guiding means 225 of a structural framework of the housing 222, be brought into a defined position within the housing 222. For easier insertion, or removing, of the cassette 233 into, or from, the housing 222, grips 228 are placed on the sides of the housing.

Cassette 233 includes a data processing unit with a microprocessor 229 and a data memory 230. As in the case of the cassette 123 described based on FIG. 2, includes the data processing unit a hardwired, or preferably wireless, interface 231, via which the data processing unit and the control unit 212 can exchange data. Especially, the control unit 212 can read out data stored in the data memory 230 concerning properties of the cassette 233. Alternatively, instead of the data processing unit, also an RFID transponder can be provided, in which these data are encoded. Then, an RFID reading device is provided, via which the control unit 212 can read out the data.

Arranged in the region of the reaction cell 234 is a temperature sensor 232. This is connected with the data processing unit for data exchange, so that the microprocessor 229 receives and processes measurement signals of the temperature sensor. The measurement signals, or therefrom derived values, can be stored in the data memory 230 or be forwarded to the control unit 212 via the interface 231. Control of the heating element can occur via the data processing unit of the cassette 233 or the central control unit 212.

Not all elements of the handling unit 203 are wear parts. Thus, components, such as, for example, pump drives or shafts, have a relatively long lifetime. It would, consequently, be uneconomic to integrate these components of the handling unit 203 into an exchangeable cassette, especially when the cassette is not going to be reconditioned after use. In the present example, consequently, only integrated into the cassette 233 are the liquid lines 216, 215, 219 221, 235, 237 embodied as hoses and parts of the liquid line 207, parts of the peristaltic pumps 208.1 and 208.2, especially the roller rotors, the hose beds, and clamp elements, which hold the hoses tight, as well as, as non-wear parts, the reaction cell 234, the data processing unit and the temperature sensor 232. The shafts 235 of the peristaltic pumps 208 are, in contrast, secured to the structural framework of the housing 222 and are not replaced with the cassette 233. Also the drives (not shown) of the peristaltic pumps 208.1 and 208.2 are integrated into the structural framework of the housing 222. The wear parts contained in the cassette are, moreover, so designed as regards their material properties that they possess a comparably long life expectancy, so that, as much as possible, no long lived component need be replaced.

By means of media detectors, which are connected with the data processing unit, so that their measurement signals can be received and processed by the data processing unit, as well as, in given cases, forwarded to the control unit 212, it can be detected, whether the peristaltic pumps 208 of the dosing, metering- and supply system 204 are still working reliably. Based on the measurement results, especially using known methods for predictive diagnosis, e.g. by extrapolation, a point in time can be ascertained, at which the cassette 233 will need to be replaced. In the case of replacement of the cassette, the same or comparable advantages, as above described based on FIG. 2, are achieved.

In the example illustrated here, the liquid storage 202 is embodied in conventional manner with individual liquid containers 214, 217, 218 and 220. It is, however, also possible to integrate the liquid storage into a second cassette, which can be connected directly via the connectors 226 with the cassette 233 in such a manner that fluid connections arise between the liquid containers and the associated liquid lines. Equally, the liquid containers 214, 217, 218 and 220 can, together with parts of the handling unit 203, be integrated into one and the same, exchangeable cassette. Also, the measuring cell 209 can be integrated into the exchangeable cassette 233. Other variations and combinations of the previously described examples of embodiments are possible.

The invention claimed is:

1. An analytical device for automated determining of a measured variable of a liquid sample, comprising:
   a liquid storage, which includes one or more liquid containers for one or more liquids;
   a measuring cell for accommodating the liquid sample, or the liquid sample to which has been added one or more liquids from said liquid storage, and a measuring arrangement for providing one or more measurement signals correlated with the measured variable;
   an electronics unit, which includes a control unit for control of the analytical device and for determining the measured variable based on the measurement signals provided by said measuring arrangement;
   a handling unit including a supply and dosing, or metering, system for supplying and metering the liquid sample and liquids from the liquid storage into the measuring cell; and
   at least one exchangeable cassette including at least a part of said liquid storage and/or a part of said handling unit associated with the liquid storage and including a cassette identifier having cassette-specific data, the cassette identifier structured to enable automated recognition of the at least one exchangeable cassette,
   wherein said control unit is configured to operate on the cassette identifier, upon connecting a new exchangeable cassette to replace said at least one exchangeable cassette, to automatically command the analytic device to perform an initializing routine at least partially based on the cassette-specific data, said initializing routine including at least one of the following steps:
   cleaning liquid contacting components of the handling unit;
   performing at least one calibration measurement;
   adjusting the analytical device based on the calibration measurement; and
   filling liquid lines of the handling unit by supplying consumable liquid from liquid containers connected with the liquid lines.

2. The analytical device as claimed in claim 1, further comprising:
   a structural framework, with which said at least one exchangeable cassette is releasably connected, and into which said measuring arrangement is integrated.

3. The analytical device as claimed in claim 1, wherein:
said at least one exchangeable cassette includes a data processing unit, including at least one data memory and a microprocessor, wherein the data memory includes the cassette-specific data and said data processing unit is integrated into a housing of said at least one exchangeable cassette.

4. The analytical device as claimed in claim 3, wherein:
said data processing unit includes an interface, via which communication, of said data processing unit with a superordinated unit is possible.

5. The analytical device as claimed in claim 2, wherein:
said at least one exchangeable cassette includes a data processing unit including at least one data memory and a microprocessor, wherein the data memory includes the cassette-specific data and said data processing unit is integrated into a housing of said at least one exchangeable cassette, and
wherein said control unit is designed, upon connection of the cassette with the structural framework, automatically or triggered by an input via an input system of said control unit, to read out data stored in said data memory of said data processing unit of said at least one cassette.

6. The analytical device as claimed in claim 2, wherein:
said at least one cassette includes guiding means, which interact with complementary guiding means of the structural framework or complementary guiding means of at least one additional cassette of the analytical device.

7. The analytical device as claimed in claim 2, wherein:
said exchangeable cassette includes maintenance requiring parts or wear parts of said handling unit; and
non-maintenance requiring parts of said handling unit are secured to said structural framework of the analytical device.

8. The analytical device as claimed in claim 1, wherein:
supplementally the measuring cell is integrated into said at least one exchangeable cassette.

9. The analytical device as claimed in claim 1, wherein:
at least two liquid containers of the liquid storage are integrated into said exchangeable cassette;
said cassette has a housing surrounding the liquid containers, and
integrated in a wall of said housing are connectors, which interact with complementary connectors of said handling unit, in order to connect liquid containers integrated into said cassette fluidically with liquid lines of the handling unit.

10. The analytical device as claimed in claim 9, wherein:
said connectors have, in each case, a closure opening or a valve opening, which is embodied in such a manner that it automatically opens upon the connecting of the liquid containers with said handling unit, and closes automatically upon the separating of the liquid containers from said handling unit.

11. The analytical device as claimed in claim 10, wherein:
said handling unit includes an adapter, which affixes the complementary connectors of said handling unit spatially in such a manner that they interact with the connectors integrated in the wall of said housing of the cassette, when the cassette is located in its intended position within the analytical device.

12. The analytical device as claimed in claim 9, wherein:
in at least one of the liquid lines of said handling unit fluidically connected with connectors of said cassette, a media detector is arranged.

13. The analytical device as claimed in claim 3, wherein:
said cassette includes at least one sensor for monitoring said cassette; and
for data exchange, said sensor is connected with the data processing unit of said cassette.

14. The analytical device as claimed in claim 13, wherein:
said at least one sensor is a temperature sensor or a fill level sensor, which is so arranged that it registers fill level in at least one liquid container.

15. The analytical device as claimed in claim 4, wherein:
said communication is wireless.

16. The analytical device as claimed in claim 4, wherein:
said superordinated unit is the control unit of the analytical device or an external servicing device or an external data processing system.

17. The analytical device as claimed in claim 7, wherein:
said wear parts comprise hoses and said maintenance requiring parts comprise drives or shafts.

18. The analytical device as claimed in claim 12, wherein:
said media detector is a light barrier.

19. The analytical device as claimed in claim 18, wherein:
said media detector is arranged in a liquid line connecting the complementary connectors of said handling unit with the supply- and dosing system.

20. An analytical device for automated determining of a measured variable of a liquid sample, comprising:
a liquid storage, which includes one or more liquid containers for one or more liquids;
a measuring cell for accommodating the liquid sample, or the liquid sample, to which has been added one or more liquids from said liquid storage, and a measuring arrangement for providing one or more measurement signals correlated with the measured variable;
an electronics unit, which includes a control unit for control of the analytical device and for determining the measured variable based on the measurement signals provided by said measuring arrangement;
a handling unit including a supply and dosing, or metering, system for supplying and metering the liquid sample and liquids from the liquid storage into the measuring cell; and
at least one exchangeable cassette including at least a part of said liquid storage and/or a part of said handling unit associated with the liquid storage and including a cassette identifier having cassette-specific data, the cassette identifier structured to enable automated recognition of the at least one exchangeable cassette,
wherein said control unit is configured to operate on the cassette identifier, upon connecting a new exchangeable cassette to replace said at least one exchangeable cassette, to automatically command the analytic device to perform an initializing routine at least partially based on the cassette-specific data.

21. The analytical device as claimed in claim 20, wherein:
said initializing routine comprising at least one of:
cleaning liquid contacting components of the handling unit;
adjusting the analytical device based on the calibration measurement; and
filling liquid lines of the handling unit by supplying consumable liquid from liquid containers connected with the liquid lines.

22. An analytical device for automated determining of a measured variable of a liquid sample, comprising:
a liquid storage, which includes one or more liquid containers for one or more liquids;
a measuring cell for accommodating the liquid sample, or the liquid sample, to which has been added one or more liquids from said liquid storage, and a measuring arrangement for providing one or more measurement signals correlated with the measured variable;
an electronics unit, which includes a control unit for control of the analytical device and for determining the measured variable based on the measurement signals provided by said measuring arrangement;
a handling unit including a supply and dosing, or metering, system for supplying and metering the liquid sample and liquids from the liquid storage into the measuring cell; and
at least one exchangeable cassette including at least a part of said liquid storage and/or a part of said handling unit associated with the liquid storage and including a data processing unit integrated into a housing of the at least one exchangeable cassette, the data processing unit including a data memory and a microprocessor, wherein the data memory includes cassette-specific data, the data processing unit configured to enable automated recognition of the at least one exchangeable cassette using the cassette-specific data,
wherein said control unit is configured to operate on the cassette-specific data provided by the data processing unit to automatically command the analytic device to perform an initializing routine after replacement of the at least one exchangeable cassette, said initializing routine at least partially based on the cassette-specific data, including the steps of:
performing at least one calibration measurement; and
adjusting the analytical device based on the calibration measurement.

23. The analytical device as claimed in claim 1, wherein:
said cassette identifier includes at least one of a data memory, an RFID-transponder or an optically readable code, said data memory, RFID-transponder or optically readable code including information concerning the exchangeable cassette; and
the control unit is further embodied to, upon replacement of the cassette, automatically or due to an input by a service person read out said information concerning the cassette from said cassette identifier.

* * * * *